US012653666B2

(12) United States Patent
Moein et al.

(10) Patent No.: US 12,653,666 B2
(45) Date of Patent: Jun. 16, 2026

(54) PACKAGING ASSEMBLY HAVING AN INJECTOR FOR INSERTING AN INTRAOCULAR LENS INTO THE CAPSULAR BAG OF AN EYE

(71) Applicant: Carl Zeiss Meditec AG, Jena (DE)

(72) Inventors: Hadi Moein, Oberkochen (DE); Annett Ortscheid, Oberkochen (DE); Martin Kelp, Oberkochen (DE)

(73) Assignee: Carl Zeiss Meditec AG, Jena (DE)

( * ) Notice: Subject to any disclaimer, the term of this patent is extended or adjusted under 35 U.S.C. 154(b) by 0 days.

(21) Appl. No.: 19/316,892

(22) Filed: Sep. 2, 2025

(65) Prior Publication Data

US 2025/0381026 A1　　Dec. 18, 2025

Related U.S. Application Data

(63) Continuation of application No. PCT/EP2024/055034, filed on Feb. 28, 2024.

(30) Foreign Application Priority Data

Mar. 1, 2023　(DE) ..................... 10 2023 105 064.8

(51) Int. Cl.
A61F 2/16　　　　(2006.01)
(52) U.S. Cl.
CPC ............ A61F 2/1691 (2013.01); A61F 2/167 (2013.01)
(58) Field of Classification Search
CPC ................................. A61F 2/1691; A61F 2/167
(Continued)

(56) References Cited

U.S. PATENT DOCUMENTS 4,862,885 A　　9/1989　Cumming
7,954,636 B2 *　6/2011　Vincent-Aubry ..... A61F 2/1678
　　　　　　　　　　　　　　　　　　　623/6.12
(Continued)

FOREIGN PATENT DOCUMENTS

CN　　　　111699014 A　　9/2020
DE　　10 2021 116 615 B3　　7/2022
(Continued)

OTHER PUBLICATIONS

International Search Report of the European Patent Office dated May 23, 2024 for international application PCT/EP2024/055034 on which this application is based.
(Continued)

*Primary Examiner* — Jacob K Ackun
(74) *Attorney, Agent, or Firm* — Walter Ottesen, P.A.

(57) ABSTRACT

A packaging assembly includes packaging and an injector for introducing an intraocular lens into the capsular sac of an eye. The injector includes: a housing having an opening for ejecting the lens in an insertion direction, a proximal end opposite the opening, and a plunger longitudinally movable in the insertion direction and configured to move the lens towards the opening. The packaging includes a distal part and a proximal part which, in a transport state, is arranged relative to the distal part different than in a use state. A driver is attached to the distal part and to the plunger so that by moving the housing counter to the insertion direction relative to the distal part, the plunger can be moved towards the opening. In the transport state, the movement of the housing counter to the insertion direction relative to the distal part is limited by the proximal part.

10 Claims, 6 Drawing Sheets

(58) Field of Classification Search
USPC ................................................. 206/363, 438
See application file for complete search history.

(56) References Cited

U.S. PATENT DOCUMENTS

| | | | | |
|---|---|---|---|---|
| 2004/0238392 | A1 | 12/2004 | Peterson et al. | |
| 2007/0168026 | A1* | 7/2007 | Nagasaka | A61F 2/1675 |
| | | | | 623/6.12 |
| 2011/0046634 | A1* | 2/2011 | Rathert | A61F 2/1678 |
| | | | | 606/107 |
| 2013/0226193 | A1 | 8/2013 | Kudo et al. | |
| 2014/0114323 | A1 | 4/2014 | Kudo et al. | |
| 2017/0119522 | A1* | 5/2017 | Auld | A61F 2/167 |
| 2019/0105151 | A1 | 4/2019 | Tseng et al. | |
| 2021/0052373 | A1 | 2/2021 | Singh et al. | |
| 2021/0093787 | A1 | 4/2021 | Perot et al. | |
| 2023/0338138 | A1 | 10/2023 | Kelp et al. | |
| 2023/0404745 | A1* | 12/2023 | Perez | A61F 2/167 |
| 2024/0108457 | A1* | 4/2024 | Kelp | A61F 2/167 |

FOREIGN PATENT DOCUMENTS

| | | |
|---|---|---|
| DE | 10 2022 109 691 B3 | 4/2023 |
| EP | 1 491 163 A2 | 12/2004 |
| WO | 2019/070282 A1 | 4/2019 |

OTHER PUBLICATIONS

English Translation and Written Opinion of the International Searching Authority dated May 23, 2024 for international application PCT/EP2024/055034 on which this application is based.

English translation and Office action of the German Patent Office dated Nov. 30, 2023 for German patent application 10 2023 105 064.8 on which the claim of priority is based.

Office Action and English Translation of the Chinese Intellectual Property Administration dated Jan. 5, 2026 for corresponding application 202480015495.7.

* cited by examiner

PACKAGING ASSEMBLY HAVING AN INJECTOR FOR INSERTING AN INTRAOCULAR LENS INTO THE CAPSULAR BAG OF AN EYE

CROSS-REFERENCE TO RELATED APPLICATIONS

This application is a continuation application of international patent application PCT/EP2024/055034, filed Feb. 28, 2024, designating the United States and claiming priority from German application 10 2023 105 064.8, filed Mar. 1, 2023, and the entire content of both applications is incorporated herein by reference.

TECHNICAL FIELD

The disclosure relates to a packaging assembly including a packaging and an injector for inserting an intraocular lens into the capsular bag of an eye.

BACKGROUND

In cataract treatment of an eye, only a small incision is usually made in the cornea of the eye, the incision being large enough to allow a tip of an injector to be inserted into the eye through the incision. Once the incision has been made in the cornea, the lens of the eye is comminuted, for example, by phacoemulsification, and then aspirated from the capsular bag of the eye. An intraocular lens is then inserted into the eye. In the process, the intraocular lens is folded such that it fits through the tip of the injector. The tip is inserted into the capsular bag through the incision, and the folded intraocular lens is pushed by a piston of the injector through the tip into the capsular bag in which the intraocular lens unfolds and thus replaces the original lens. Before the injector can be used, the injector has to be prepared. For this purpose, in particular, a piston of the injector has to be moved so far that the intraocular lens is moved from a storage state of the intraocular lens, in which the intraocular lens is substantially free of mechanical tension, into the tip of the injector and is thus folded. A movement of the piston and thus a movement of the intraocular lens out of the storage state before the cataract treatment is carried out must be avoided, because storing the intraocular lens in a folded state over a long period of time can lead to irreversible deformation of the intraocular lens.

SUMMARY

It is an object of the disclosure to provide a packaging assembly including a packaging and an injector, wherein an irreversible deformation of an intraocular lens arranged in the injector can be avoided with the packaging assembly.

The packaging assembly according to the disclosure includes a packaging and an injector, the latter being configured to insert an intraocular lens into the capsular bag of an eye. The injector has an injector housing with an injector opening, via which the intraocular lens is movable out of the injector in an insertion direction of the injector, a proximal end arranged away from the injector opening, and a piston which is mounted in the injector housing longitudinally movably in the insertion direction and is configured to move the intraocular lens in a direction toward the injector opening. The packaging has a transport state and a use state and also has a distal packaging part and a proximal packaging part which, in the transport state, is arranged relative to the distal packaging part differently than in the use state. The packaging has a driver which is mounted on the distal packaging part and is coupled to the piston, such that, by a movement of the injector housing relative to the distal packaging part counter to the insertion direction, the piston is movable in the direction of the injector opening. In the transport state, the movement of the injector housing relative to the distal packaging part counter to the insertion direction is limited by the proximal packaging component. The packaging is configured such that the movement of the injector housing relative to the distal packaging part counter to the insertion direction is carried out or made possible via the packaging being brought from the transport state to the use state.

Since the movement of the injector housing in the transport state is limited counter to the insertion direction, the piston cannot move the intraocular lens toward the injector opening. As a result, the intraocular lens cannot be folded in the transport state, which folding could lead to the intraocular lens deforming irreversibly. Only when the packaging is brought from the transport state to the use state can the injector housing be moved counter to the insertion direction. For example, this can be done by bringing the packaging from the transport state to the use state or, in the use state, by moving the injector housing by hand relative to the distal packaging part counter to the insertion direction. Since the packaging has the driver, it is advantageously not necessary to provide an additional component on which the driver is arranged. In order to prepare the injector for cataract treatment, it is always necessary to remove the injector from the packaging. In the packaging assembly according to the disclosure, this automatically leads to the piston being moved toward the injector opening. This can advantageously cut out a step in the preparation of the injector for cataract treatment.

According to various embodiments, it is preferred that the proximal packaging part has a base of the proximal packaging part and an elevation of the proximal packaging part, which elevation rises from the base of the proximal packaging part and is configured such that, in the transport state, the proximal end abuts the elevation of the proximal packaging part and thus the movement of the injector housing relative to the distal packaging part counter to the insertion direction is limited. Alternatively or in addition, it is conceivable that the proximal packaging part has a stop elevation, which rises from the base of the proximal packaging part and is configured such that, in the transport state, a component of the injector different than the proximal end abuts the stop elevation and thus limits the movement of the injector housing relative to the distal packaging part counter to the insertion direction. The component of the injector different than the proximal end can be, for example, a handle of the injector.

According to various embodiments, the proximal packaging part is preferably attached pivotably to the distal packaging part, so that the packaging can be brought from the transport state into the use state by a pivoting of the proximal packaging part relative to the distal packaging part, wherein, in the use state, the movement of the injector housing relative to the distal packaging part counter to the insertion direction is not limited by the elevation of the proximal packaging part and/or the stop elevation. Thus, in the use state, the movement of the injector housing relative to the distal packaging part counter to the insertion direction is possible.

Alternatively, the proximal packaging part can be attached pivotably to the distal packaging part; it is preferred that the proximal packaging part is attached movably to the distal packaging part. The injector has a projection which protrudes from the injector transversely with respect to the insertion direction, wherein the elevation of the proximal packaging part is configured and/or the proximal packaging part has a further elevation of the proximal packaging part, which further elevation is configured such that the elevation of the proximal packaging part and/or the further elevation of the proximal packaging part strikes against the projection when the proximal packaging part is moved away from the distal packaging part counter to the insertion direction, as a result of which the elevation of the proximal packaging part and/or the further elevation of the proximal packaging part drives the projection and thus the injector housing counter to the insertion direction. The projection can be, for example, a thumb rest of the injector, which thumb rest is to be contacted by a thumb of one hand in order to move the piston in the insertion direction. In another example, the projection can be a handle of the injector.

According to various embodiments, it is preferred that the packaging has a bellows, via which the proximal packaging part is arranged movably on the distal packaging part. Alternatively or additionally, the packaging preferably has a web with a first longitudinal end, which is fastened to the distal packaging part, and a second longitudinal end, which is arranged on the proximal packaging part, wherein the web is curved more strongly in the transport state than in the use state. Thus, the packaging can be brought from the transport state to the use state via a deformation of the web. Alternatively or additionally, the distal packaging part and the proximal packaging part form a plain bearing, via which the proximal packaging part is mounted movably on the distal packaging part.

According to various embodiments, it is preferred that the base of the proximal packaging part and the elevation of the proximal packaging part delimit a proximal recess, wherein, in the transport state, the proximal end is arranged in the proximal recess. The proximal recess may be accessible in a mounting direction perpendicular to the insertion direction. Thus, for assembling the packaging assembly, the injector can be inserted into the proximal recess in the mounting direction.

According to various embodiments, the distal packaging part preferably has a base of the distal packaging part and an elevation of the distal packaging part, which elevation rises from the base of the distal packaging part, wherein the base of the distal packaging part and the elevation of the distal packaging part delimit a distal recess in which, in the transport state, a distal end of the injector facing away from the proximal end is arranged. The distal recess may be accessible in the mounting direction. Thus, in order to assemble the packaging assembly, the injector can be inserted into the distal recess in the mounting direction.

According to various embodiments, it is preferred that the injector housing has a housing opening via which, in the transport state, the driver extends into the interior of the injector housing and is there coupled to the piston. In particular, the housing opening can be arranged spaced apart from the injector opening.

According to various embodiments, the packaging assembly preferably includes the intraocular lens which, in the storage state, is arranged within the injector housing. In particular, the intraocular lens in the storage state is substantially free of mechanical stress and/or unfolded.

BRIEF DESCRIPTION OF DRAWINGS

The invention will now be described with reference to the drawings wherein.

DETAILED DESCRIPTION

Figure 1:
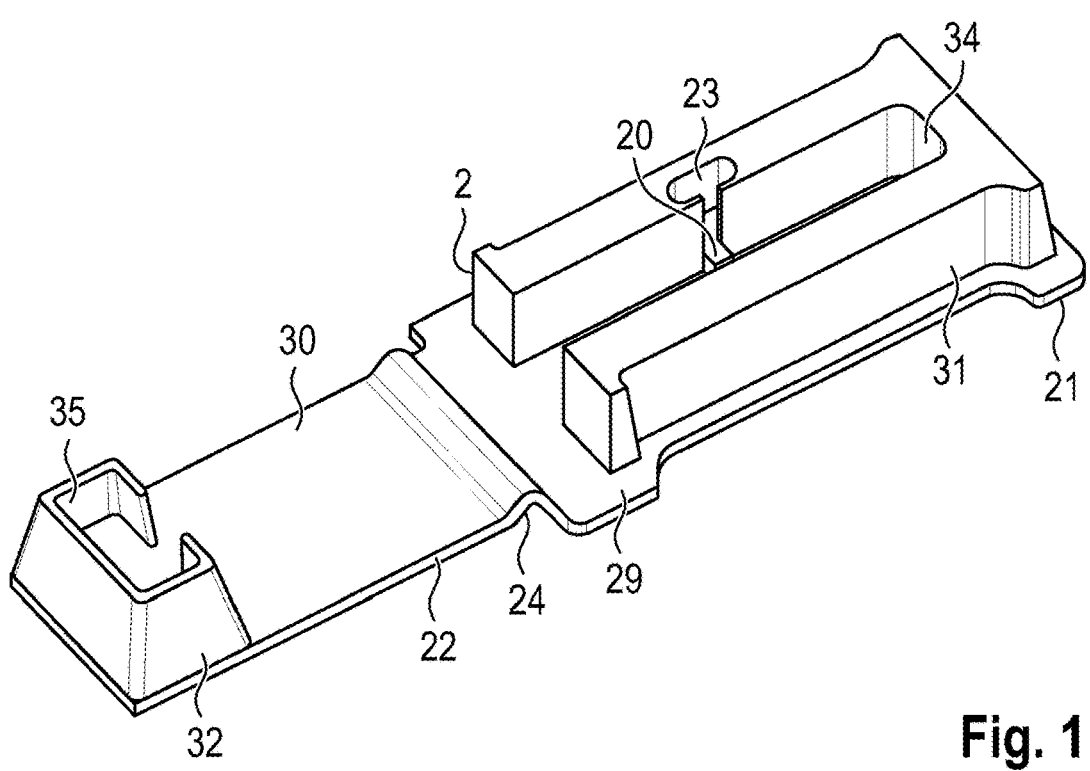
FIG. 1 shows a perspective view of a first embodiment of a packaging.
Figure 2:
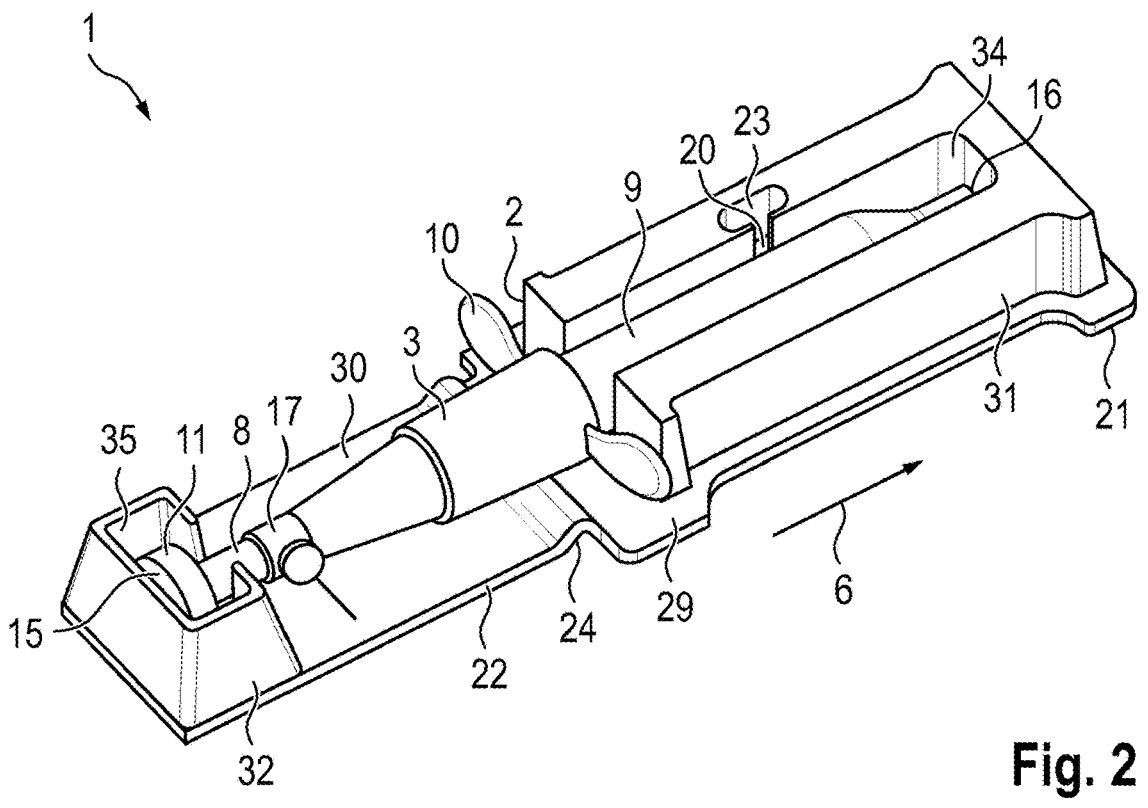
FIG. 2 shows a perspective view of a first embodiment of a packaging assembly with an injector and the packaging from FIG. 1 in a storage state of the packaging.
Figure 3:
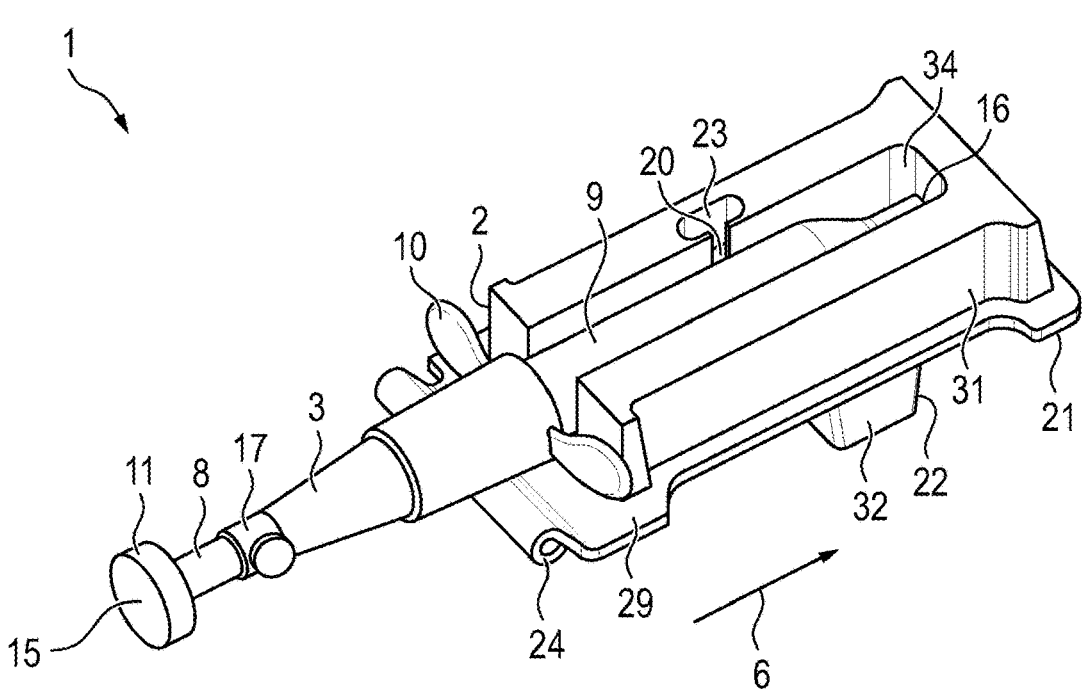
FIG. 3 shows a perspective view of the first embodiment of the packaging assembly in a use state of the packaging.
Figure 4:
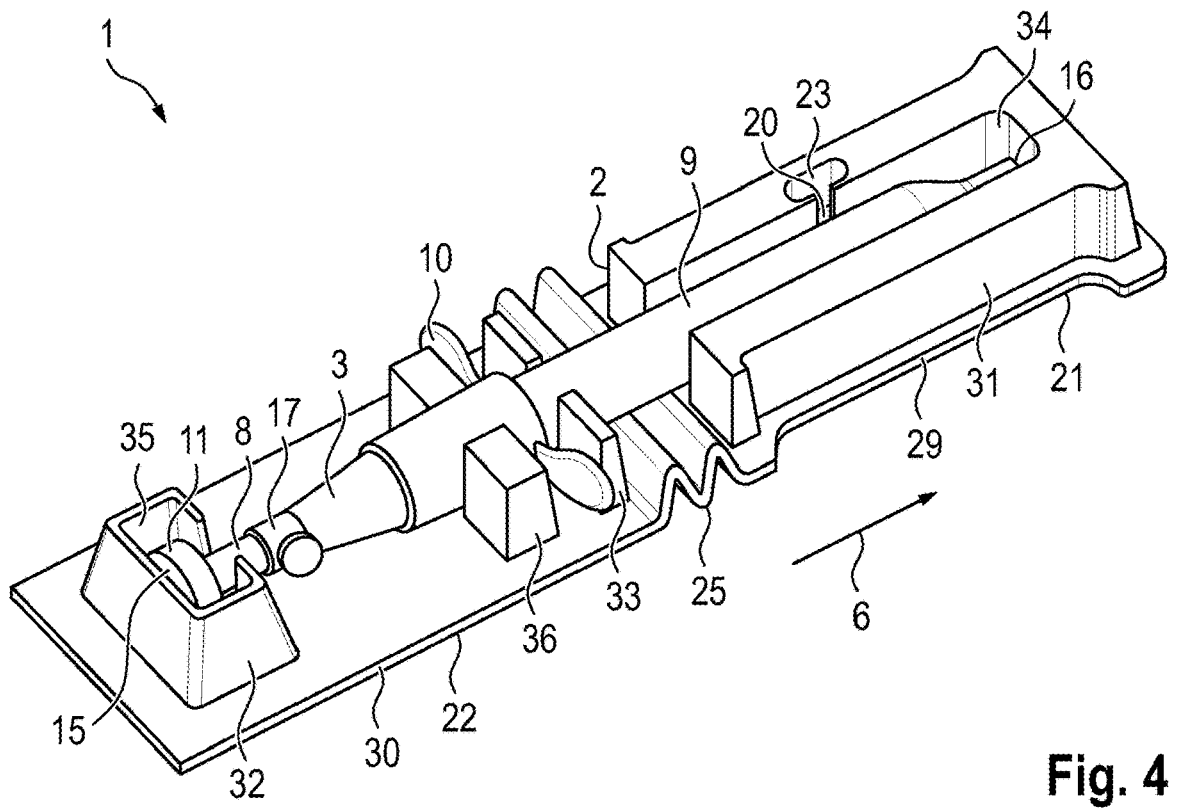
FIG. 4 shows a perspective view of a second embodiment of the packaging assembly having a second embodiment of the packaging.

As can be seen from FIGS. 2 to 4, a packaging assembly 1 includes a packaging 2 and an injector 3, the latter being configured to insert an intraocular lens 4 (see FIGS. 7 to 9) into the capsular bag of an eye. FIGS. 2 to 4 and 7 to 9 show that the injector 3 has an injector housing 9 with an injector opening 5 (see FIGS. 7 to 9) via which the intraocular lens 4 is movable out of the injector 3 in an insertion direction 6 of the injector 3. In addition, the injector 3 has a proximal end 15 (see FIGS. 1 to 9), arranged away from the injector opening 5, and a piston 7 (see FIGS. 7 to 9) which is mounted longitudinally movably in the injector housing 9 in the insertion direction 6 and is configured to move the intraocular lens 4 in a direction toward the injector opening 5, in particular to move it in the insertion direction 6 toward the injector opening 5. The packaging 2 has a transport state (see FIGS. 1, 2, 4 and 5) and a use state (see FIG. 3) and also has a distal packaging part 21 and a proximal packaging part 22 which, in the transport state, is arranged relative to the distal packaging part 21 differently than in the use state. The packaging 2 has a driver 20 (see FIGS. 1 to 5 and 7 to 9) which is mounted on the distal packaging part 21 and is coupled to the piston 7, such that, by a movement of the injector housing 9 relative to the distal packaging part 21 counter to the insertion direction 6, the piston 7 is movable in the direction of the injector opening 5. In the transport state, the movement of the injector housing 9 relative to the distal packaging part 21 counter to the insertion direction 6 is limited by the proximal packaging component 22. The packaging 2 is configured such that the movement of the injector housing 9 relative to the distal packaging part 21 counter to the insertion direction 6 is carried out (see FIGS. 4 to 6) or made possible (see FIGS. 1 to 3) via the packaging 2 being brought from the transport state to the use state. It is conceivable that the packaging assembly 1 has the intraocular lens 4 which, in the storage state, is arranged within the injector housing 9. In particular, the intraocular lens 4 in the storage state can be substantially free of mechanical stress and/or unfolded.

FIGS. 2 to 4 show that the injector 3 can have a thumb rest 11 which is to be contacted by a thumb of one hand when the piston 7 is moved by the hand in the direction of the injector opening 5. The thumb rest 11 can form the proximal end 15. In addition, it can be seen from FIGS. 2 to 4 that the injector 3 can have a handle 10 which, during the movement of the piston 7, is to be gripped by fingers of the hand other than the thumb. The handle 10 can be arranged spaced apart from the proximal end 15 and spaced apart in the insertion direction 6 from the injector opening 5.

Figure 5:
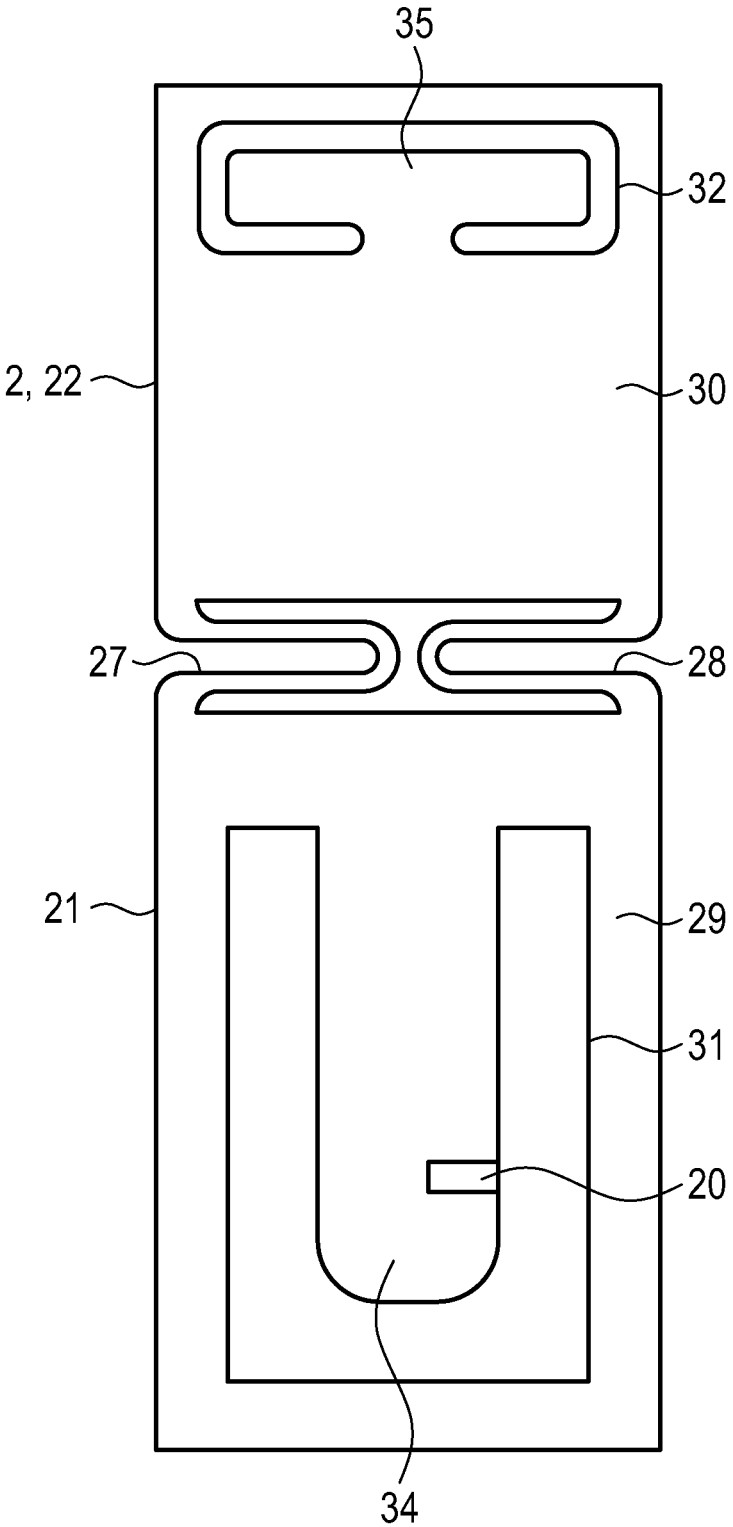
FIG. 5 shows a plan view of a third embodiment of the packaging.
Figure 6:
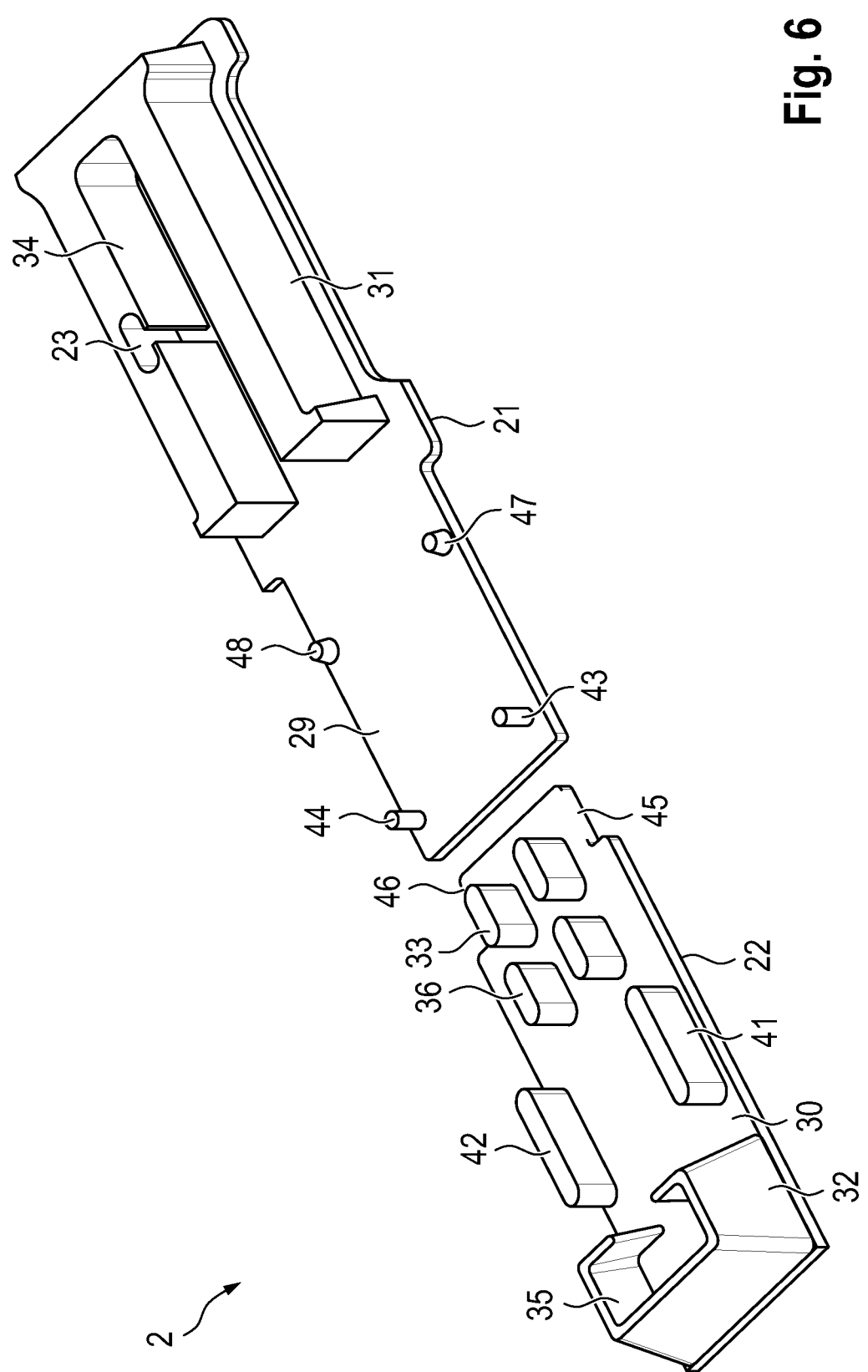
FIG. 6 shows a perspective view of a fourth embodiment of the packaging.

FIGS. 1 to 6 show that the proximal packaging part 22 can have a base 30 of the proximal packaging part 22 and an elevation 32 of the proximal packaging part 22, which elevation rises from the base 30 of the proximal packaging part 22 and is configured such that, in the transport state, the proximal end 15 abuts the elevation 32 of the proximal packaging part 22 and thus the movement of the injector housing 9 relative to the distal packaging part 21 counter to the insertion direction 6 is limited. Alternatively or in addition, it is conceivable, as shown in FIGS. 4 and 6, that the proximal packaging part 22 has a stop elevation 36, which rises from the base 30 of the proximal packaging part 22 and is configured such that, in the transport state, a component of the injector 3 different than the proximal end 15 abuts the stop elevation 36 and thus limits the movement of the injector housing 9 relative to the distal packaging part 21 counter to the insertion direction 6. The component of the injector 3 different than the proximal end 15 can be, for example, the handle 10.

FIGS. 1 to 3 show that the proximal packaging part 22 is mounted pivotably on the distal packaging part 21, so that the packaging 2 can be brought from the transport state shown in FIGS. 1 and 2 to the use state shown in FIG. 3 by a pivoting of the proximal packaging part 22 relative to the distal packaging part 21. In the use state, the movement of the injector housing 9 relative to the distal packaging part 21 counter to the insertion direction 6 is not limited by the elevation 32 of the proximal packaging part 22 and/or the stop elevation 36. FIGS. 1 to 3 show that the packaging 2 can have a film hinge 24, via which the proximal packaging part 22 is mounted pivotably on the distal packaging part 21. However, other joints are also conceivable, such as a joint in which a pin engages in a sleeve and is mounted rotatably in the sleeve. After the packaging 2 has been pivoted from the storage state into the use state, the movement of the injector housing 9 relative to the distal packaging part 21 counter to the insertion direction 6 is possible, because the elevation 32 of the proximal packaging part 22 no longer blocks the proximal end 15 and/or the stop elevation 36 no longer blocks the component different than the proximal end 15, in particular the handle 10; compare FIG. 3.

FIGS. 4 to 6 show that the proximal packaging part 22 can be mounted on the distal packaging part 21 so as to be movable, in particular longitudinally movable, counter to the insertion direction 6, and that the injector 3 can have a projection which protrudes from the injector 3 transversely with respect to the insertion direction 6. The elevation 32 of the proximal packaging part 22 can be configured such that the elevation 32 of the proximal packaging part 22 strikes against the projection when the proximal packaging part 22 is moved away from the distal packaging part 21 counter to the insertion direction 6 and drives the projection and thus the injector housing 9 counter to the insertion direction 6. The projection can be the thumb rest 11 for example. Alternatively or additionally, the proximal packaging part 22 can have a further elevation 33 of the proximal packaging part 22, which further elevation is configured such that the further elevation 33 of the proximal packaging part 22 strikes against the projection when the proximal packaging part 22 is moved away from the distal packaging part 21 counter to the insertion direction 6 and drives the projection and thus the injector housing 9 counter to the insertion direction 6. In this case, the projection can be formed, for example, by the handle 10; cf. FIG. 4. Alternatively or additionally, the projection in this case can be formed by the thumb rest 11.

The packaging 2 can have a bellows 25 (see FIG. 4), via which the proximal packaging part 22 is arranged movably on the distal packaging part 21. In the transport state, the bellows 25 can be in its compressed state, and, in the use state, the bellows 25 can be in its stretched state.

FIG. 5 shows that the packaging 2 can have a web 27 with a first longitudinal end, which is fastened to the distal packaging part 21, and a second longitudinal end, which is arranged on the proximal packaging part 22, wherein the web 27 is curved more strongly in the transport state than in the use state. In addition, it is conceivable that the packaging 2 has a further web 28 with a first longitudinal end, which is fastened to the distal packaging part 21, and a second longitudinal end, which is arranged on the proximal packaging part 22, wherein the further web 28 is curved more strongly in the transport state than in the use state. For example, via the distal packaging part 21 being gripped with one hand and the proximal packaging part 22 being gripped with another hand, and then both hands being moved away from each other, the web 27 and optionally the further web 28 can be deformed and the packaging can be brought from the storage state to the use state.

FIG. 6 shows that the distal packaging part 21 and the proximal packaging part 22 form a plain bearing, via which the proximal packaging part 22 is mounted movably on the distal packaging part 21. For example, for this purpose, the packaging 2 can have a slide elevation 41, which delimits an interior space, and a slide 43, which is arranged longitudinally movably in the interior space. For example, the slide elevation 41 can be arranged on the proximal packaging part 22 and the slide 43 can be arranged on the distal packaging part 21, as shown in FIG. 6. Alternatively, the slide elevation 41 can be arranged on the distal packaging part 21 and the slide 43 can be arranged on the proximal packaging part 22. In addition, it is conceivable that the packaging 2 can have a further slide elevation 42, which delimits a further interior space, and a further slide 44, which is arranged longitudinally movably in the further interior space.

The distal packaging part 21 can have a pin 47 and optionally a further pin 48, which in the storage state abut the proximal packaging part 22 and thus limit a movement of the proximal packaging part 22 relative to the distal packaging part 21 in the insertion direction 6; see FIG. 6. It is conceivable that the proximal packaging part 22 has, for each of the pins 47, 48, a respective recess 45, 46. Alternatively, the proximal packaging part 22 can have a pin and optionally a further pin, which in the storage state abut the distal packaging part 21 and thus limit a movement of the proximal packaging part 22 relative to the distal packaging part 21 in the insertion direction 6. It is conceivable that the distal packaging part 21 has, for each of the pins, a respective recess.

Figure 7:
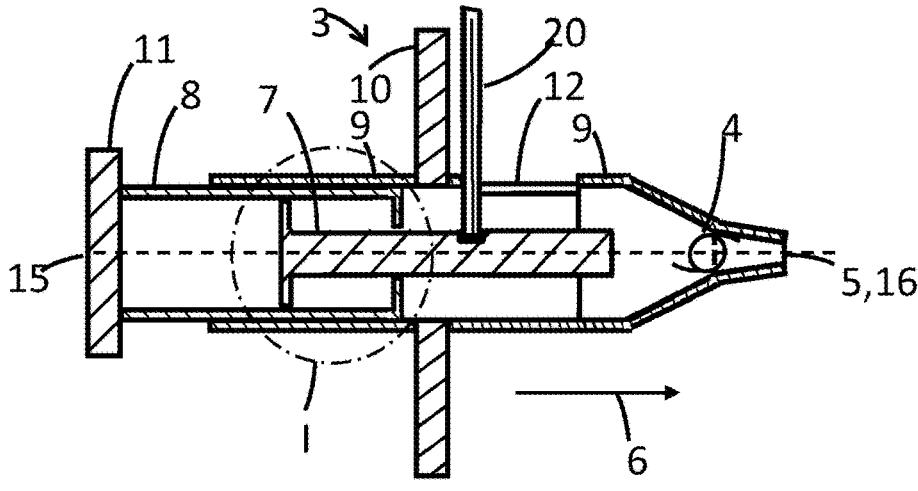
FIG. 7 shows a longitudinal section through an injector of the packaging assembly at a first point in time.
Figure 8:
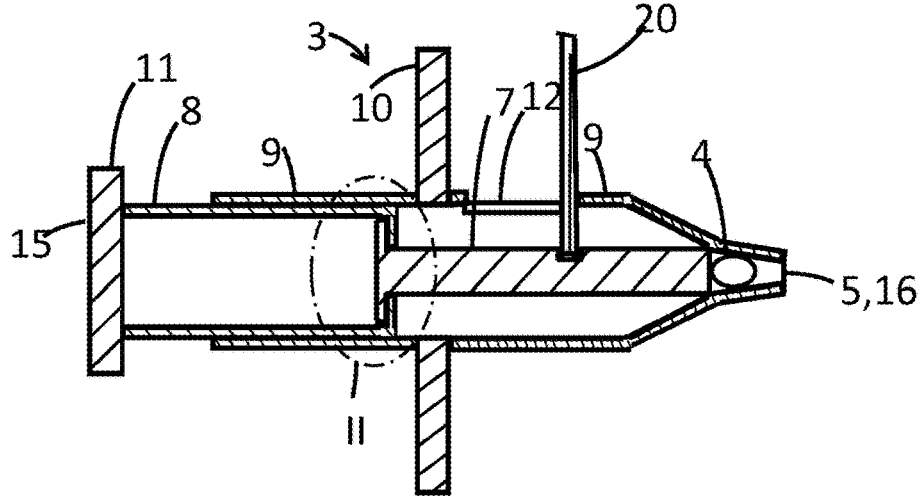
FIG. 8 shows the longitudinal section from FIG. 7 at a second point in time.
Figure 9:
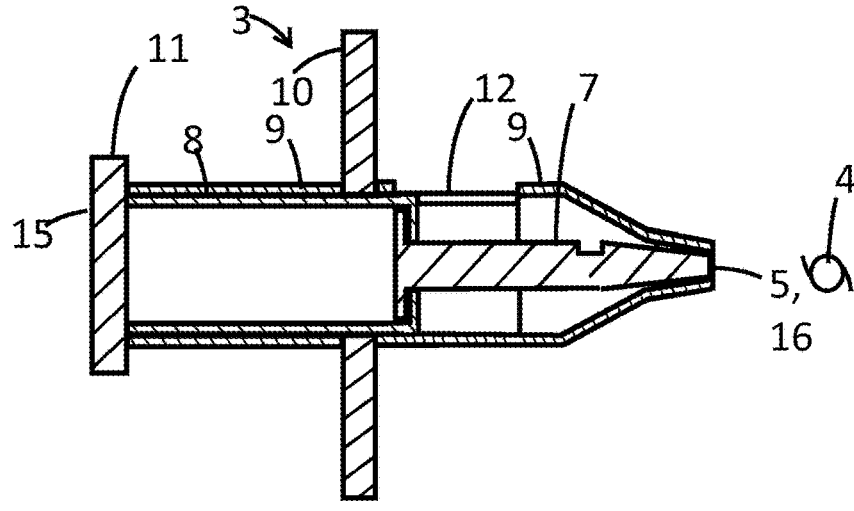
FIG. 9 shows the longitudinal section from FIG. 7 at a third point in time.

FIGS. 1 to 6 show that the base 30 of the proximal packaging part 22 and the elevation 32 of the proximal packaging part 22 can delimit a proximal recess 35, with FIGS. 2 and 4 showing that in the transport state the proximal end 15 can be arranged in the proximal recess 35. The proximal recess 35 can be accessible in a mounting direction perpendicular to the insertion direction 6. Thus, for assembling the packaging assembly 1, the injector 3 can be inserted into the proximal recess 35 in the mounting direction. FIGS. 1 to 6 also show that the distal packaging part 21 can have a base 29 of the distal packaging part 21 and an elevation 31 of the distal packaging part 21, which elevation rises from the base 29 of the distal packaging part 21, wherein the base 29 of the distal packaging part 21 and the elevation 31 of the distal packaging part 21 delimit a distal recess 34 in which is arranged, in the transport state, a distal end 16 of the injector 3 arranged facing away from the proximal end 15. The distal recess 34 can be accessible in the mounting direction. Thus, for assembling the packaging assembly 1, the injector 3 can be inserted into the proximal recess 35 in the mounting direction. It is conceivable that the elevation 31 of the distal packaging part 21 forms an interference fit for an end region of the injector 3, wherein the end region has the distal end 16. For example, the interference fit can be formed such that a force of less than 5 N is required to remove the end region from the packaging 2. FIGS. 7 to 9 also show that the injector opening 5 can be arranged at the distal end 16.

FIGS. 7 to 9 show that the injector housing 9 can have a housing opening 12 via which, in the transport state, the driver 20 extends into the interior of the injector housing 9 and is there coupled to the piston 7. The housing opening 12 can be arranged separately from the injector opening 5.

The distal packaging part 21 can have a groove 23 with an undercut (see FIGS. 1 to 4 and 6) into which the driver 20 is inserted in order to secure the driver 20 to the distal packaging part 21. Alternatively, the driver 20 can be glued to the distal packaging part 21 and/or welded (see FIG. 5), and/or the driver 20 can be formed as a projection from the distal packaging part 21.

FIGS. 7 to 9 show that the injector 3 can have a further piston 8, which is mounted longitudinally movably in the injector housing 9, in particular in the insertion direction 6. The piston 7 and the further piston 8 can either be in a decoupling state (see FIG. 7), in which the piston 7 and the further piston 8 are longitudinally movable relative to each other, or in a coupling state (see FIGS. 8 and 9), in which the piston 7 and the further piston 8 are rigidly coupled to each other in the insertion direction 6 and the total longitudinal extent of the piston 7 and of the further piston 8 in the insertion direction 6 is longer than in the decoupling state. FIG. 7 shows the injector 3 in the decoupling state. Via the piston 7 being moved toward the injector opening 5 on account of the movement of the injector housing 9 relative to the distal packaging part 21 counter to the insertion direction 6, the piston 7 and the further piston 8 are brought into the coupling state and the intraocular lens 4 can be brought into a folded state; cf. FIG. 8. Subsequently, when the injector 3 is arranged outside the packaging 2, the piston 7 and the further piston 8 can be moved together in the insertion direction 6, and the intraocular lens 4 can thus be moved out of the injector 3 via the injector opening 5; cf. FIG. 9. The thumb rest 11 can be attached to the further piston 8 for this purpose. By provision of the further piston 8, the injector 3 can be shorter than if only the piston 7 were provided.

As can be seen from FIGS. 2 and 3, the injector 3 can have a lock 17, which has a locking state, in which a movement of the further piston 8 in the insertion direction 6 is limited, and an unlocking state, in which the movement of the further piston 8 in the insertion direction 6 is not limited. For example, the lock 17 can have a ring which is arranged externally on the further piston 8 and outside the injector housing 9 and which is configured to strike against the injector housing 9 in the locking state. In order to bring the lock 17 into the unlocking state, the ring can be removed from the further piston 8.

Figure 10:
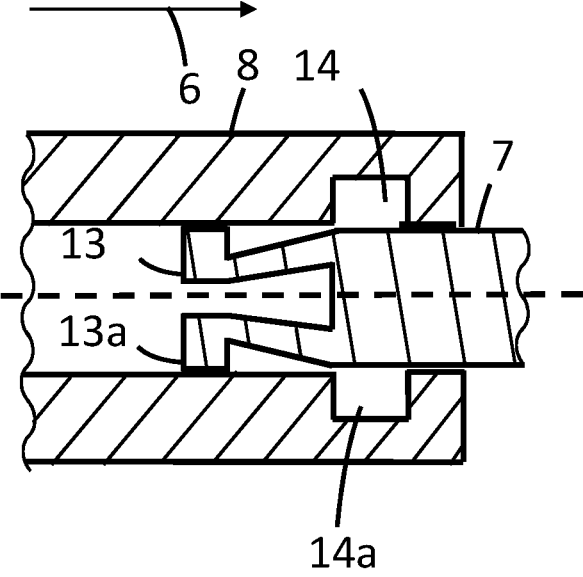
FIG. 10 shows an illustration of a detail I from FIG. 7, wherein a piston and a further piston of the injector are in a decoupling state; and, FIG. 11 shows an illustration of a detail II from FIG. 8, wherein the piston and the further piston are in a coupling state.
Figure 11:
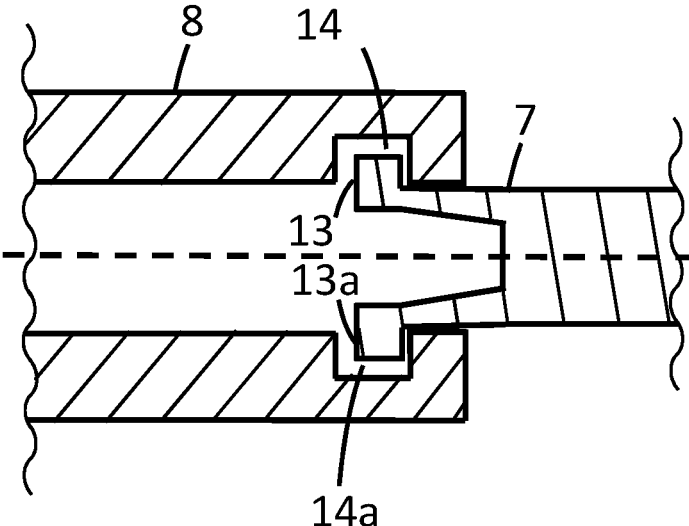

FIGS. 7 to 11 show that the further piston 8 can have a cavity, and the piston 7 in the decoupling state can be arranged longitudinally movably in the cavity. FIGS. 10 and 11 show that the piston 7 can have a piston projection 13 and the further piston 8 can have a piston recess 14, wherein the piston projection 13 is configured to be arranged outside the piston recess 14 when the piston 7 and the further piston 8 are in the decoupling state (see FIG. 10), and, for bringing the piston 7 and the further piston 8 into the coupling state, is configured to engage in the piston recess 14 (see FIG. 11) when the piston 7 is moved toward the injector opening 5. FIGS. 10 and 11 moreover show that the piston 7 can have a further piston projection 13*a* and the further piston 8 can have a further piston recess 14*a*, wherein the further piston projection 13*a* is configured to be arranged outside the further piston recess 14*a* when the piston 7 and the further piston 8 are in the decoupling state (see FIG. 10), and, for bringing the piston 7 and the further piston 8 into the coupling state, is configured to engage in the further piston recess 14*a* (see FIG. 11) when the piston 7 is moved toward the injector opening 5.

It is conceivable that the packaging 2 has a film (not shown in the figures) which is attached to the distal packaging part 21 and the proximal packaging part 22 in the storage state and, together with the distal packaging part 21 and the proximal packaging part 22, forms a closed packaging cavity in which the injector 3 is arranged. After the film has been removed from the distal packaging part 21 and the proximal packaging part 22, it is conceivable to wet the intraocular lens 4 with physiological saline solution and/or an ophthalmic viscoelastic device (OVD). This can be done, for example, via the housing opening 12 or via an opening in the injector housing 9 different than the housing opening 5. Thereafter, it is conceivable to bring the packaging 2 from the transport state into the use state.

It is understood that the foregoing description is that of the preferred embodiments of the invention and that various changes and modifications may be made thereto without departing from the spirit and scope of the invention as defined in the appended claims.

LIST OF REFERENCE SIGNS

1 Packaging assembly
2 Packaging
3 Injector
4 Intraocular lens
5 Injector opening
6 Insertion direction
7 Piston
8 Further piston
9 Injector housing
10 Handle
11 Thumb rest
12 Housing opening
13 Piston projection
13*a* Further piston projection
14 Piston recess
14*a* Further piston recess
15 Proximal end
16 Distal end
17 Lock
20 Driver

21 Distal packaging part
22 Proximal packaging part
23 Groove
24 Film hinge
25 Bellows
27 Web
28 Further web
29 Base of the distal packaging part
30 Base of the proximal packaging part
31 Elevation of the distal packaging part
32 Elevation of the proximal packaging part
33 Further elevation of the proximal packaging part
34 Distal recess
35 Proximal recess
36 Stop elevation
41 Slide elevation
42 Further slide elevation
43 Slide
44 Further slides
45 Recess
46 Further recess
47 Pin
48 Further pin

The invention claimed is:

1. A packaging assembly comprising:
a packaging;
an injector configured to insert an intraocular lens into a capsular bag of an eye;
said injector including an injector housing defining an injector opening via which the intraocular lens is movable out of said injector in an insertion direction of said injector;
said injector having a proximal end arranged away from said injector opening;
said injector having a piston mounted in said injector housing longitudinally movably in the insertion direction and configured to move the intraocular lens in a direction toward said injector opening;
said packaging having a transport state and a use state;
said packaging further having a distal packaging part and a proximal packaging part which, in said transport state, is arranged relative to said distal packaging part differently than in said use state;
said packaging having a driver which is attached to said distal packaging part and is coupled to said piston so that, by a movement of said injector housing relative to said distal packaging part counter to said insertion direction, said piston is movable in the direction of said injector opening; and,
wherein, in said transport state, the movement of said injector housing relative to said distal packaging part counter to said insertion direction is limited by said proximal packaging part and said packaging is configured such that movement of said injector housing relative to said distal packaging part counter to said insertion direction is carried out or made possible via said packaging being brought from said transport state to said use state.

2. The packaging assembly of claim 1, wherein said proximal packaging part has a base of said proximal packaging part and an elevation of said proximal packaging part; and, said elevation rises from said base of said proximal packaging part and is configured such that, in said transport state, said proximal end abuts said elevation of said proximal packaging part and thus the movement of said injector housing relative to said distal packaging part counter to said insertion direction is limited.

3. The packaging assembly of claim 2, wherein said proximal packaging part is attached pivotably to said distal packaging part so that said packaging can be brought from said transport state into said use state by a pivoting of said proximal packaging part relative to said distal packaging part; and, in said use state, the movement of said injector housing relative to said distal packaging part counter to said insertion direction is not limited by said elevation of said proximal packaging part.

4. The packaging assembly of claim 2, wherein said proximal packaging part is attached movably to said distal packaging part; said injector has a projection which protrudes from said injector transversely with respect to said insertion direction; said elevation of said proximal packaging part is configured and/or said proximal packaging part has a further elevation of the proximal packaging part, which further elevation is configured such that said elevation of said proximal packaging part and/or said further elevation of said proximal packaging part abuts said projection when said proximal packaging part is moved away from said distal packaging part counter to said insertion direction, as a result of which said elevation of said proximal packaging part and/or said further elevation of said proximal packaging part drives said projection and thus said injector housing counter to said insertion direction.

5. The packaging assembly of claim 4, wherein said packaging has a bellows via which said proximal packaging part is arranged movably on said distal packaging part.

6. The packaging assembly of claim 4, wherein said packaging has a web with a first longitudinal end fastened to said distal packaging part and a second longitudinal end arranged on said proximal packaging part; and, said web is curved more strongly in said transport state than in said use state.

7. The packaging assembly of claim 4, wherein said distal packaging part and said proximal packaging part form a plain bearing, via which said proximal packaging part is mounted movably on said distal packaging part.

8. The packaging assembly of claim 2, wherein said base of said proximal packaging part and said elevation of said proximal packaging part delimit a proximal recess; and, in said transport state, said proximal end is arranged in said proximal recess.

9. The packaging assembly of claim 1, wherein said distal packaging part has a base of said distal packaging part and an elevation of said distal packaging part; said elevation of said distal packaging part rises from said base of said distal packaging part; and, said base of said distal packaging part and said elevation of said distal packaging part delimit a distal recess in which is arranged, in said transport state, a distal end of said injector arranged facing away from said proximal end.

10. The packaging assembly of claim 1, wherein said injector housing has a housing opening via which, in said transport state, said driver extends into an interior of said injector housing and is there coupled to said piston.

\* \* \* \* \*